US00PP08246P

United States Patent [19]

van der Knaap

[11] Patent Number: Plant 8,246

[45] Date of Patent: Jun. 1, 1993

[54] CHRYSANTHEMUM PLANT NAMED AUTUMN EYES

[75] Inventor: Jack van der Knaap, Ax De Lier, Netherlands

[73] Assignee: Fides Beheer B.V., De Lier, Netherlands

[21] Appl. No.: 712,334

[22] Filed: Jun. 7, 1991

[51] Int. Cl.[5] ..... A01H 5/00

[52] U.S. Cl. ..... Plt./82.2

[58] Field of Search ..... Plt./74, 74.1, 82.2, Plt./78

[56] References Cited

U.S. PATENT DOCUMENTS

P.P. 6,299 9/1988 van der Knaap ..... Plt. 74

P.P. 6,300 9/1988 van der Knaap ..... Plt. 74

P.P. 6,777 5/1989 Hesse ..... Plt. 74

*Primary Examiner*—Howard J. Locker

*Attorney, Agent, or Firm*—Burns, Doane, Swecker & Mathis

[57] ABSTRACT

A new and distinct variety of Chrysanthemum plant. The new plant is characterized by its flat capitulum form, anemone capitulum type, bronze ray floret color, darker contrasting disc floret color, a diameter across face of capitulum of ca. 3.4 cm, spreading to upright branching pattern with ca. 4.0 breaks after a single pinch, flowering response of 59 to 63 days from the start of short days, and plant height for a 6.5 in. (16.5 cm) pot of about 30–40 cm. with 1–2 applications of B-9 at 2500 ppm.

1 Drawing Sheet

BACKGROUND

1. The Field of the Invention

This invention relates to Chrysanthemum plants. More particularly, the present invention comprises a new and distinct cultivar of Chrysanthemum plant, botanically known as *Dendranthema grandiflora* and hereinafter referred to by the cultivar name "Autumn Eyes".

2. Background of the New Plant

Autumn Eyes, identified as 86.2494, was originated from a cross made by Jack Van Der Knaap in a controlled breeding program at De Lier, Holland in 1985.

The female parent of Autumn Eyes was an unnamed seedling, and the male parent was Penny Lane (U.S. Plant Pat. No. 6,238).

Autumn Eyes was discovered and selected as one flowering plant within the progeny of the stated cross by Jack Van Der Knaap in 1986 in a controlled environment at De Lier, Holland.

The first asexual reproduction of Autumn Eyes was accomplished when vegetative cuttings were taken in 1986 in a controlled environment at De Lier, Holland by technicians working under the direction and supervision of Jack Van Der Knaap.

SUMMARY OF THE INVENTION

The basic characteristics which have been repeatedly observed in Autumn Eyes and which, in combination, distinguish this Chrysanthemum plant over related known varieties and its antecedents are:

1. Flat capitulum form.
2. Anemone capitulum type.
3. Bronze ray floret color.
4. Darker contrasting disc floret color.
5. Diameter across face of capitulum ca. 3.4 cm.
6. Branching pattern is spreading to upright with ca. 4.0 breaks after a single pinch.
7. Flowering response is 59 to 63 days from the start of short days.

8. Plant height of a 6.5 in. (16.5 cm) pot is about 30–40 cm. with 1–2 applications of B-9 at 2500 ppm.

Horticultural examination of controlled flowerings of successive plantings has shown that the combination of characteristics and distinctions as herein disclosed for Autumn Eyes are firmly fixed and are retained through successive generations of asexual reproduction.

DETAILED DESCRIPTION OF THE NEW PLANT

Figure 1:
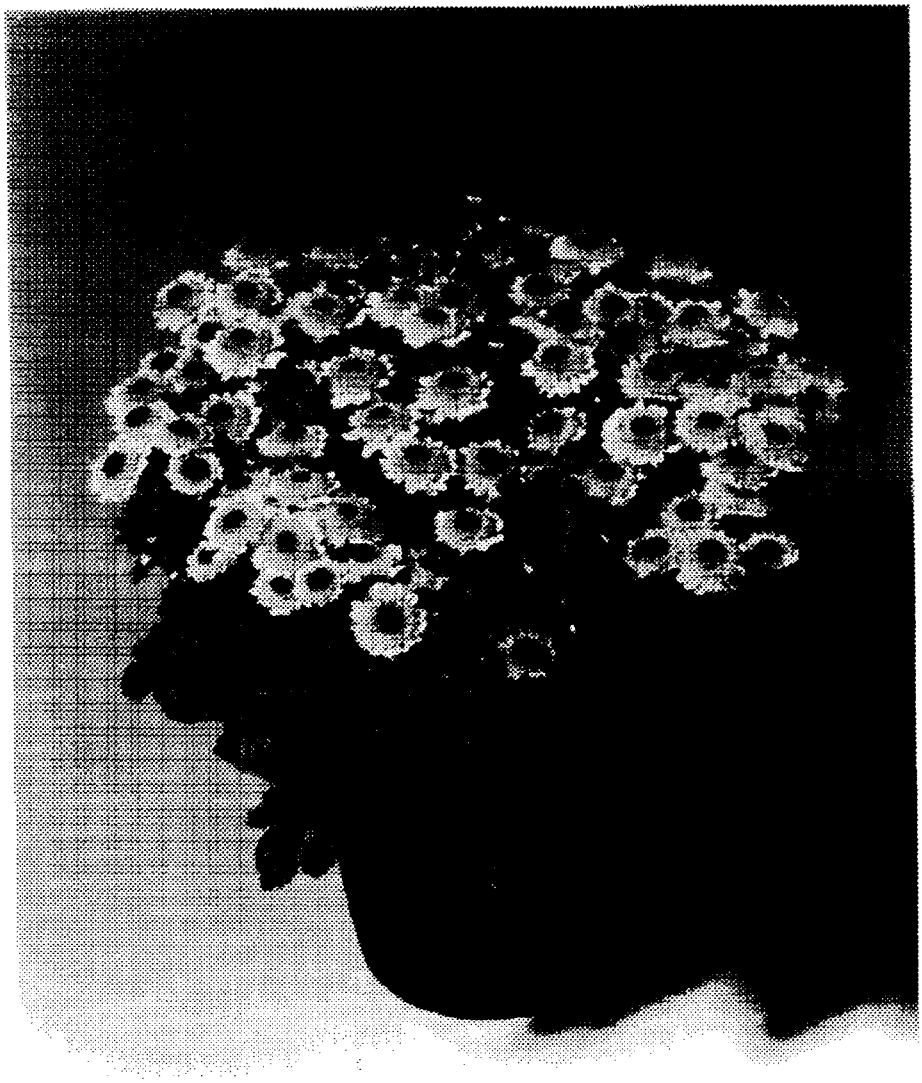
FIG. 1 is a photographic print in full color showing typical inflorescence and leaf characteristics of Autumn Eyes grown as a pinched spray pot mum with 5 cuttings in a 6.5 inch (16.5 cm) pot, the colors being depicted as nearly true as it is reasonably possible to make the same in a color photograph of this character.

Autumn Eyes has not been observed under all possible environmental conditions. The phenotype may vary significantly with variations in environment such as temperature, light intensity, and day length.

The following is a detailed description of Autumn Eyes, with color terminology in accordance with The Royal Horticulture Society Colour Chart, except where general color terms of ordinary dictionary significance are obvious. The following observations, measurements and comparisons were made of plants grown at Nipomo, Calif., in controlled environments. Unrooted cuttings were directly stuck into 6.5 inch (16.5 cm) pots and grown in a controlled environment under the natural temperature and day length prevailing during October to December of 1990.

Classification:

*Botanical.*—*Dendranthema grandiflora* cv. Autumn Eyes.

*Commercial.*—Flat anemone to be grown as a spray pot or cut spray mum.

INFLORESCENCE

A. Capitulum:

*Form.*—Flat.

*Type.*—Anemone.

*Diameter across face.*—ca. 34 mm when fully opened.

B. Corolla of ray florets:

*Color (general tonality from a distance of three meters).*—Bronze yellow with dark maroon eye.

*Color.*—Front: Golden yellow 11 A. Back: Pale yellow 11 B.

*Shape.*—Oblong with rounded to flat tip.

C. Corolla of disc florets:

*Color.*—Golden 11 A tipped with dark maroon 59 A. Eye is dark maroon 59 A.

D. Reproductive organs:

*Androecium.*—Present on disc florets only; insignificant.

*Gynoecium.*—Present on both ray and disc florets; insignificant.

PLANT

A. General appearance:

*Height.*—When grown in 6.5 in. (16.5 cm) pots with 1-2 applications of B-9, the total plant height including the pot will be approximately 40 cm. When grown as a cut mum, the plant will be 1-1.5 meters high.

*Branching pattern.*—Upright to spreading with ca. 4.0 breaks after the pinch. As a cut flower the plant is normally grown unpinched, single stem with the top bud removed to form an open spray type form.

B. Foliage

*Color (upper surface).*—147 A.

*Color (lower surface).*—147 B.

*Shape.*—see FIG. 1.

Autumn Eyes can be well distiguished from other commercial Chrysanthemum cultivars, including Dark Eyes (U.S. Plant patent application Ser. No. 712,903, filed Jun. 7, 1991). Definite Eyes (U.S. Plant patent application No. 712,086, filed Jun. 7, 1991), Quiet Eyes (U.S. Plant patent application No. 712,052, filed Jun. 7, 1991), Tara (U.S. Plant Pat. No. 6,313), and Vibrant Eyes (U.S. Plant patent application Ser. No. 712,901, filed Jun. 7, 1991). See in this regard the data presented in Table A hereafter. Also, the blossom coloration of Autumn Eyes can be readily distinguished from Hoof Lane (U.S. Plant Pat. No. 6,299), Main Lane (U.S. Plant Pat. No. 6,300), and Bourbon Street (U.S. Plant Pat. No. 6,777) as described in the respective U.S. Plant patents.

Similar traits to the other above-mentioned Eye varieties are capitulum form and type (with the exception of Quiet Eyes which is a flat daisy type), branching pattern, and the distinctly contrasting center of the disc. However, each Eye variety varies in color of the disc and ray florets, making each a unique and different cultivar.

Similar traits to Tara are capitulum form and type, and breaks/pinch. Autumn Eyes generally has more disc florets per flower, is approximately 4-7 days slowers, has more and shorter and narrower ray florets, and fewer flowers per break than Tara. The coloration of the petals is very different between Tara and Autumn Eyes.

TABLE A

| Characteristic | Autumn Eyes | Dark Eyes | Definite Eyes |
|---|---|---|---|
| capitulum form | flat | flat | flat |
| capitulum type | anemone | anemone | anemone |
| diameter across face | ca. 3.4 cm | ca. 3.5-6.0 cm | 4.0-7.0 cm |
| branching pattern | upright | spreading | upright and spreading |
| breaks/pinch | ca. 4.0 | 4-7 | 3-5 |
| height in 6.5 in. (16.5 cm) pot with 1-2 applications of B-9 | 30-40 cm | ca. 40 cm | 40-52 cm |
| disc floret color | golden 11 A tipped with dark maroon 59 A; eye is dark maroon 59 A | medium lavender 75 C graduating to a very dark eye of 77 A; tube 75 C | 56 C on the outer petals graduating to a dark purple eye of 59 A |
| no. disc florets | ca. 171 | ca. 145 | ca. 255 |
| length disc florets | ca. 1.0 cm long | 1.0-1.5 cm long | up to 2 cm long |
| ray floret color | front: golden yellow 11 A back: pale yellow 11 B | front: 75 C back: 75 C with a 77 B stripe down the center | front: 69 D back: some 70 C |
| no. ray florets | ca. 22 | 24-27 | average of 27.3 |
| shape ray florets | oblong with rounded to flat tip | oblong with rounded tip | elliptic |
| length ray florets | 1.0-1.5 cm long | up to 2.5 cm long | up to 4 cm long |
| width ray florets | 0.3-0.5 cm wide | up to 0.75 cm wide | up to 1.0 cm wide |
| no. flowers/break | ca. 9.6 | average of 5.16 | average of 5.3 |
| leaf color | front: 147 A back: 147 B | front: 147 A back: 147 B | front: 147 A back: 147 B |
| leaf length | ca. 7.5 cm long | up to 8 cm long | up to 6 cm long |
| leaf width | ca. 5.0 cm wide | up to 4.5 cm wide | up to 4 cm wide |
| response time | 8.5 weeks | 8.5 weeks | 8.5 weeks |

| Characteristic | Quiet Eyes | Tara | Vibrant Eyes |
|---|---|---|---|
| capitulum form | flat | flat | flat fresh; puffy rounded old |
| capitulum type | daisy | anemone | anemone |
| diameter across face | 8-10 cm | 5.0-6.5 cm | 3-4 cm |
| branching pattern | spreading | spreading | upright to spreading |
| breaks/pinch | 3-4 | 3-5 | 4-5 |
| height in 6.5 in. (16.5 cm) pot with 1-2 applications of B-9 | ca. 40 cm | ca. 37 cm | 42-52 cm |
| disc floret color | lemon yellow 1 A graduating to a large green eye of 143 A | lemon yellow 10 A | from 155 D graduating toward a dark purple eye of 77 A |
| no. disc florets | ca. 200 | 70-120 | ca. 125 |
| length disc florets | 1.3 cm long | up to 1.5 cm long | ca. 1 cm long |
| ray floret color | front: 75 B back: 75 D | front: 155 A back: 155 D | light pink to white; front: 155 A back: 155 B bright green ovary |
| no. ray florets | 20-24 | 15-17 | ca. 22 |
| shape ray florets | oblong | elliptic | oval with rounded tip |

TABLE A-continued

| | | | |
|---|---|---|---|
| length ray florets | up to 4 cm long | up to 3 cm long | up to 1.7 cm long |
| width ray florets | up to 1.5 cm wide | up to 1 cm wide | up to 0.5 cm wide |
| no. flowers/ break | ca. 5.2 | ca. 11.3 | ca. 8.4 |
| leaf color | front: 147 A<br>back: 147 B | front: 147 A<br>back: 147 B | front: 147 A<br>back: 147 B |

TABLE A-continued

| | | | |
|---|---|---|---|
| leaf length | up to 10 cm long | up to 9 cm long | up to 5.0 cm long |
| leaf width | up to 5.5 cm wide | up to 5 cm wide | up to 3.0 cm wide |
| response time | 8.2 weeks | 8.0 weeks | 8.0 weeks |

I claim:

1. A new and distinct variety of Chrysanthemum plant, substantially as herein described and illustrated.

* * * * *